United States Patent

Kojima et al.

Patent Number: 5,124,325
Date of Patent: Jun. 23, 1992

[54] THERAPEUTIC AGENTS OF METABOLIC BONE DISEASE

[75] Inventors: Eisuke Kojima, Koga; Koji Saito, Oyama, both of Japan

[73] Assignee: Kyorin Pharmaceutical Co., Ltd., Tokyo, Japan

[21] Appl. No.: 536,007

[22] Filed: Jun. 8, 1990

[30] Foreign Application Priority Data

Jun. 13, 1989 [JP] Japan ................. 1-149988

[51] Int. Cl.$^5$ ...................... A61K 31/54; A61K 31/47
[52] U.S. Cl. ................. 514/224.2; 514/230.5; 514/311; 514/312
[58] Field of Search ............... 544/105, 52, 160, 162, 544/163; 546/165, 166; 514/224.2, 230.5, 311, 312

[56] References Cited

U.S. PATENT DOCUMENTS 4,956,372  9/1990  Kojima et al. ................. 546/165

FOREIGN PATENT DOCUMENTS 0310096  4/1989  European Pat. Off. .

*Primary Examiner*—John M. Ford
*Assistant Examiner*—Y. N. Gupta
*Attorney, Agent, or Firm*—Oblon, Spivak, McClelland, Maier & Neustadt

[57] ABSTRACT

New use of cyclic anthranilic acid derivatives of the following formula,

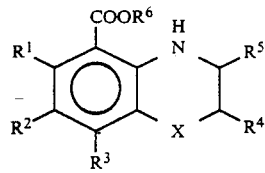

wherein $R^1$, $R^2$ and $R^3$ each independently indicate a hydrogen atom, chlorine atom, lower alkyl group having 1 to 3 carbon atoms, lower alkoxy group having 1 to 3 carbon atoms, amino group, nitro group, hydroxy group, sulfonamide group, trifluoromethyl group, cyano group, carboxyl group, carbamoyl group, acetyl group, benzoymethyl group which may be substituted, methylthio group, phenylethnyl group which may be substituted, alkanoylamino group having 1 to 3 carbon atoms, benzoylamino group which may be substituted, alkylsulfonylamino group having 1 to 3 carbon atoms or phenylsulfonylamino group which may be substituted; $R^4$ and $R^5$ each independently indicate a hydrogen atom, lower alkyl group having 1 to 3 carbon atoms, cyano group, carboxyl group, hydroxymethyl group, phenyl group which may be substituted or benzoyl group, $R^6$ indicates a hydrogen atom, lower alkyl group having 1 to 3 carbon atoms or benzyl group; X indicates a methylene group, oxygen atom, sulfur atom, sulfinyl group or sulfonyl group, their acid or alkali salts thereof as therapeutic agents for metabolic bone diseases is described.

1 Claim, No Drawings

THERAPEUTIC AGENTS OF METABOLIC BONE DISEASE

DETAILED DESCRIPTION OF THE INVENTION

This invention is concerned with new use of cyclic anthranilic acid derivatives, their acid and alkali salts thereof which have therapeutic effects on metabolic bone diseases and inhibitory effects on bone resorption.

Metabolic bone diseases as generic term include osteoporosis, osteomalacia and ostetic fibrous. In patients with these diseases, there are morbid changes in weight, constitution and structure of bone as a result of the failure of systemic bone formation and resorption process. This is caused by the abnormalities in the somatological regulatory system due to various hormones or vitamins, and by the congenital or acquired abnormalities of the functions of the osteocytes. It is also associated with abnormal calcium and phosphorus metabolism. Vitamin D, calcium, calcitonin and phosphorus are used as therapeutic agents, but their effectiveness has not been clearly proven and development of a superior drug has been strongly desired.

It has been reported that 3-phenyl-4H-1-benzopyran-4-one derivative (Ipriflavone) and 2-phenyl-4H-1-benzopyran-4-one derivative have inhibitory effect on bone resorption and may be useful as therapeutic agents for osteoporosis. However, their efficacy is not sufficient as therapeutic agents for metabolic bone diseases.

Previously, we have found that cyclic anthranilic acid derivatives represented by a general formula (I), their acid or alkali salts thereof have immunomodulatory activity and high potency for induction of suppressor T cells, and have therapeutic effects on adjuvant arthritis (Japanese Patent Application No. 236295/88 which corresponding to Japan Kokai 279867/89 and EP-A-0 310 096).

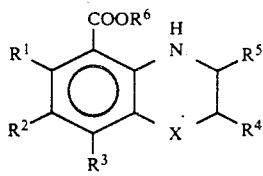

wherein $R^1$, $R^2$ and $R^3$ each independently indicate a hydrogen atom, chlorine atom, lower alkyl group having 1 to 3 carbon atoms, lower alkoxy group having 1 to 3 carbon atoms, amino group, nitro group, hydroxy group, sulfonamide group, trifluoromethyl group, cyano group, carboxyl group, carbamoyl group, acetyl group, benzoylmethyl group which may be substituted, methylthio group, phenylethynyl group which may be substituted, alkanoylamino group having 1 to 3 carbon atoms, benzoylamino group which may be substituted, alkylsulfonylamino group having 1 to 3 carbon atoms or phenylsulfonylamino group which may be substituted; $R^4$ and $R^5$ each independently indicate a hydrogen atom, lower alkyl group having 1 to 3 carbon atoms, cyano group, carboxyl group, hydroxymethyl group, phenyl group which may be substituted or benzoyl group, $R^6$ indicates a hydrogen atom, lower alkyl group having 1 to 3 carbon atoms or benzyl group; X indicates a methylene group, oxygen atom, sulfur atom, sulfinyl group or sulfonyl group.

Further to our previous finding, we have found that the compounds represented by the general formula (I) have unexpectedly high potency to inhibit bone resorption, safe enough, and are useful as therapeutic agents for metabolic bone diseases. Among the compounds represented by the general formula (I), we show typical examples that support the usefulness of the present invention. These example compounds can be synthesized by the method reported in Japan Kokai 279867/89 (EP-A-0 310 096).

TABLE 1

(I)

| Compound No. | X | $R^1$ | $R^2$ | $R^3$ | $R^4$ | $R^5$ | $R^6$ |
|---|---|---|---|---|---|---|---|
| 1 | $CH_2$ | H | Cl | H | H | Ph | H |
| 2 | $CH_2$ | H | H | H | H | Ph | H |
| 3 | $CH_2$ | H | $NO_2$ | H | H | H | H |
| 4 | $CH_2$ | H | Cl | H | H | H | H |
| 5 | $CH_2$ | H | H | H | Ph | H | H |
| 6 | $CH_2$ | H | H | H | H | –C₆H₄–OH | H |
| 7 | $CH_2$ | H | TsNH | H | H | Ph | H |
| 8 | $CH_2$ | H | H | H | H | –C₆H₄–OCH(CH₃)₂ | H |

Ts: p-toluenesulfonyl

Experiment 1

Inhibition of bone resorption $^{45}$Ca prelabeled rat embryonic limbs for the measurement of bone resorption were prepared by the method of Raisz (J. Clin. Invest. 44, 103 (1965)). Briefly, 17th day pregnant SD rats were injected subcutaneously with 200 μCi of calcium-45 as calcium chloride. Two days later, the rats were killed, the embryos removed and washed with sterilized phosphated buffer solution (PBS). The forelimbs were dissected free of muscle and the cartilagious ends were cut off. The bone shaft was cultured with BGJb medium containing 20% bovine serum albumin (BSA).

The effect of each example compound of this invention on bone resorption was assessed by the method of Tsuda et al (J. Bone & Mineral Res. 1, 207 (1986)) with slight modification. Briefly, the trimmed bone was precultured for 24 hours at 37 °C. and in an atmosphere of 5% $CO_2$ in air on a millipore filter immersed in 0.6 ml of BGJb medium containing 20% BSA. 24-well plate was used for culture. The bone on the filter was then transferred to a new well filled with the medium containing the compounds of this invention with or without IL-1β and cultured for 72 hours. 0.3 ml of the supernatant was collected and used to determine the $^{45}$Ca release from the bone. The bone was immersed in 0.3 ml of 1 N HCl for not less than 90 minutes, and 10 ml of ACS II scintillator was added so as to measure the radioactivity in a liquid scintillation counter. The activity of bone resorption was expressed as percent of $^{45}$Ca release to supernatant from labeled bone (sum of the radioactivity of the bone and the medium). One bone was cultured on one well and each experimental group consisted of 5 or 6 bones derived from fetus in one pregnant rat. The activity of bone resorption was determined by the formula.

TABLE 1

$$\text{Inhibition (\%)} = \frac{C - T}{C - U} \times 100$$

U: $^{45}$Ca release without adding IL-1$\beta$
C: $^{45}$Ca release by adding IL-1$\beta$
T: $^{45}$Ca release by adding IL-1$\beta$ and example compound

| Compound No. | Concentration (μg/ml) | Inhibition (%) |
|---|---|---|
| 1 | 25 | 74 |
| 2 | 25 | 113 |
| 3 | 25 | 100 |
| 4 | 25 | 76 |
| 5 | 25 | 103 |
| 6 | 25 | 70 |
| 7 | 25 | 80 |
| 8 | 25 | 92 |
| Ipriflavone* | 25 | 58 |

*7-isopropoxyisoflavone

The compounds of this invention represented by the general formula (I) markedly inhibited bone resorption, and thus are very useful as the therapeutic agents for metabolic bone diseases.

The following examples will illustrate the synthesis method of the compound used in above experiment.

REFERENTIAL EXAMPLE 1

5,6-Dihydro-4H-pyrrolo[3,2,1-ij]quinoline-1,2-dione

To a solution of 1,2,3,4-tetrahydroquinoline (18.5 g) in anhydrous tetrahydrofuran (THF; 150 ml) was added a solution of oxalyl chloride (22 ml) in anhydrous THF (100 ml) dropwise under reflux and reflux was continued for 3.5 hours. After cooling, the reaction mixture was concentrated under reduced pressure. To the resulting residue was added carbon disulfide (800 ml) and refluxed under stirring. To the refluxing mixture was added aluminum chloride (35 g) portionwise during 5 hours, further refluxed for 3 hours and then allowed to stand for overnight. To the reaction mixture, under cooling, was added concentrated hydrochloric acid (150 ml) and then water (150 ml), extracted with chloroform. The organic layer was washed with water, dried over anhydrous sodium sulfate and concentrated under reduced pressure. The resulting residue was recrystallized from ethanol to give the title compound (21 g, 80%) as dark reddish needles, mp 198°-200 ° C.

REFERENTIAL EXAMPLE 2

8-Nitro-5,6-dihydro-4H-pyrrolo[3,2,1-ij]quinoline-1,2-dione

5,A powder of 6-dihydro-4H-pyrrolo[3,2,1-ij]quinoline-1,2-dione (5 g) was added portionwise to nitric acid fuming (20 ml) under cooling below 0 ° C. and stirring. Further stirred for an hour, the reaction mixture was allowed to stand in a refrigerator for overnight. The reaction mixture was poured into ice-water, the resulting precipitate was collected by filtration and washed with water. The precipitate was dried and recrystallized from ethanol-n-hexane to give the title compound (3.8 g, 61%) as orange crystals, mp 198°-199 ° C.

REFERENTIAL EXAMPLE 3

8-Chloro-5,6-dihydro-4-phenyl-4H-pyrrolo[3,2,1-ij]quinoline-1,2-dione

A mixture of 5,6-dihydro-4-phenyl-4H-pyrrolo[3,2,1-ij]-quinoline-1,2-dione (3.1 g) and N-chlorosuccinimide (1.89 g) in dimethylformamide (DMF; 50 ml) was stirred at 80 ° C. for an hour. After cooling, the mixture was concentrated under reduced pressure and to the resulting residue was added chloroform (500 ml). The organic layer was washed with water and saturated aqueous sodium chloride solution, dried over sodium sulfate and concentrated under reduced pressure to give the title compound (3.4 g, 96.8%). This crystals was recrystallized from acetonitrile to give dark reddish crystals, mp 173°-174 ° C.

Using the procedure described above, compounds shown in table 3 were prepared.

TABLE 3

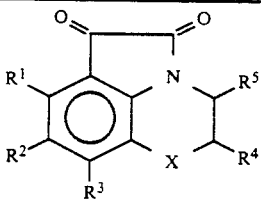

(II)

| Referential example | X | R$^1$ | R$^2$ | R$^3$ | R$^4$ | R$^5$ | Yield (%) | Mp (°C.) |
|---|---|---|---|---|---|---|---|---|
| 4 | CH$_2$ | H | H | H | H | Ph | 78.3 | 129-130 (A) |
| 5 | CH$_2$ | H | H | H | Ph | H | 49.2 | 131-132 (A) |
| 6 | CH$_2$ | H | Cl | H | H | H | 47.4 | 188-189 (A) |
| 7 | CH$_2$ | H | H | H | H | 4-OH—Ph | 96.8 | Oily |
| 8 | CH$_2$ | H | NO$_2$ | H | H | Ph | 99.4 | 184-185 (A) |

Recryst. solvent A: acetonitrile.

EXAMPLE 1

6-Chloro-2-phenyl-1,2,3,4-tetrahydroquinoline-8-carboxylic acid

To a solution of 8-chloro-5,6-dihydro-4-phenyl-4H-pyrrolo-[3,2,1-ij]quinoline-1,2-dione (3.4 g) and sodium hydroxide (2 g) in water (100 ml) was added 35% aqueous hydrogen peroxide solution (5 ml) and stirred at room temperature for an hour. The reaction mixture was acidified slightly by adding concentrated hydrochloric acid, the resulting precipitate was collected by filtration, washed and dried to give the title compound (3.17 g, 96.7%) as yellow crystals. This crystals was recrystallized from ethanol to pale yellow needles, mp 199°-200 ° C.

Analysis (%) for $C_{16}H_{14}ClNO_2$, Calcd. (Found): C, 66.79 (66.83); H, 4.90 (4.96); N, 4.87 (4.89).

Using the procedure described above, compound shown in table 4 were prepared.

TABLE 4

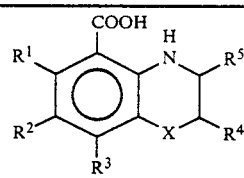

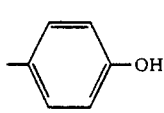

| Ex. | X | $R^1$ | $R^2$ | $R^3$ | $R^4$ | $R^5$ | Yield (%) | Mp (°C.) | Analysis (%) Calcd./Found C | H | N |
| --- | --- | --- | --- | --- | --- | --- | --- | --- | --- | --- | --- |
| 2 | $CH_2$ | H | H | H | H | Ph | 92.6 | 190 (A) | 75.87 75.52 | 5.97 5.93 | 5.54 5.43 |
| 3 | $CH_2$ | H | $NO_2$ | H | H | Ph | 80 | 256–258 (A) | 54.05 54.11 | 4.54 4.55 | 12.61 12.70 |
| 4 | $CH_2$ | H | H | H | Ph | H | 29.5 | 198–200 (A) | 75.87 75.57 | 5.97 6.01 | 5.53 5.31 |
| 5 | $CH_2$ | H | Cl | H | H | H | 61.4 | 213–215 (A) | 56.74 56.74 | 4.76 4.71 | 6.62 6.60 |
| 6 | $CH_2$ | H | H | H | H | -C6H4-OH | 24 | 172–173 (B) | 71.36 70.93 | 5.61 5.63 | 5.20 5.08 |

Recryst. solvent A: Ethanol, B: Ethyl acetate-n-hexane.

EXAMPLE 7

2-Phenyl-6-p-toluenesulfonylamino-1,2,3,4-tetrahydroquinoline-8-carboxylic acid (a) Methyl 2-phenyl-6-amino-1,2,3,4-tetrahydroquinoline-8-carboxylate To a solution of 6-nitro-2-phenyl-1,2,3,4-tetrahydroquinoline-8-carboxylic acid in DMF (100 ml) was added potassium carbonate (8.3 g) and methyl iodide (5.5 ml) and stirred at room temperature for 2 hours. After the insoluble materials were filtered off, the filtrate was concentrated under reduced pressure and to the resulting residue was added ethyl acetate (500 ml). The organic layer was washed with water and saturated aqueous sodium chloride solution successively, dried over sodium sulfate and concentrated under reduced pressure to give the brown crystals (8.65 g, 93.9%).

This crystals were dissolved in DMF-ethanol (1:1, 300 ml), to the solution was added 10% palladium-charcoal (1 g) and stirred at room temperature and hydrogen atmosphere for 5 hours. The catalysts were filtered off, the filtrate was concentrated under reduced pressure to give the title compound (6.97 g, 89.3%).

(b) 2-Phenyl-6-p-toluenesulfonylamino-1,2,3,4-tetrahydroquinoline-8-carboxylic acid Methyl 2-phenyl-6-amino-1,2,3,4-tetrahydroquinoline-8-carboxylate (3.5 g) was dissolved in dioxane (80 ml). To the solution was added p-toluenesulfonyl chloride (2.84 g) and triethylamine (2.1 ml) and stirred at room temperature for 3 hours. To the reaction mixture was added water (300 ml), extracted with ethyl acetate and washed with saturated aqueous sodium chloride solution. The organic layer was dried over anhydrous sodium sulfate and concentrated under reduced pressure. The resulting residue was purified by silica gel column chromatography (eluting with ethyl acetate:n-hexane=1:3) to give the pale yellow crystals (3.75 g, 69.4%).

This crystals were dissolved in ethanol (50 ml). To the solution was added sodium hydroxide (2 g) and water (20 ml) and refluxed for 3 hours. To the reaction mixture was added water (300 ml), acidified by adding concentrated hydrochloric acid and resulting precipitate was collected by filtration. The precipitate was washed with water and dried to give the title compound (3 g, 82.6%). This crystals were recrystallized from ethanol to give the pale yellow crystals, mp 219°–220 ° C.

Analysis (%) for $C_{23}H_{22}N_2O_4S$, Calcd. (Found): C, 65.38 (65.29); H, 5.25 (5.18); N, 6.63 (6.56).

EXAMPLE 8

2-(4-Isopropoxyphenyl)-1,2,3,4-tetrahydroquinoline-8-carboxylic acid

The compound of example 6 (810 mg) was dissolved in DMF (15 ml). To the solution was added potassium carbonate (1 g) and isopropyl iodide (1.07 g) and stirred at room temperature for 22 hours. After the insoluble materials were filtered off, the filtrate was concentrated under reduced pressure and to the resulting residue was added ethyl acetate-benzene (1:1, 200 ml). The organic layer was washed with water and saturated aqueous sodium chloride solution successively, dried over anhydrous sodium sulfate and concentrated under reduced pressure to give the yellow oily materials (930 mg, 87.8%).

This oily materials were dissolved in ethanol (10 ml). To the solution was added 1N-aqueous sodium hydroxide solution (5 ml) and refluxed for 5 hours. After cooling, to the reaction mixture was added water (50 ml) and acidified by adding 1N-hydrochloric acid. The resulting precipitate was collected by filtration, washed with water and dried to give the title compound (730 mg, 89.1%). This crystals were recrystallized from ethyl acetate-n-hexane to give the yellow crystals, mp 166°–167 ° C.

Analysis (%) for $C_{19}H_{21}NO_3$, Calcd. (Found): C, 73.29 (73.24); H, 6.80 (6.80); N, 4.50 (4.39).

What is claimed is:

1. A method of inhibiting bone resorption in a patient in need thereof, which comprises administering to said patient an effective amount of at least one cyclic anthranilic acid derivative of the following formula (I),

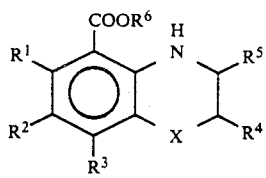

wherein $R^1$, $R^2$ and $R^3$ each independently indicate a hydrogen atom, chlorine atom, lower alkyl group having 1 to 3 carbon atoms, lower alkoxy group having 1 to 3 carbon atoms, amino group, nitro group, hydroxy group, sulfonamide group, trifluoromethyl group, cyano group, carboxyl group, carbamoyl group, acetyl group, benzoylmethyl group which may be substituted, methylthio group, phenylethynyl group which may be substituted, alkanoylamino group having 1 to 3 carbon atoms, benzoylamino group which may be substituted, alkylsulfonylamino group having 1 to 3 carbon atoms or phenylsulfonylamino group which may be substituted; $R^4$ and $R^5$ each independently indicate a hydrogen atom, lower alkyl group having 1 to 3 carbon atoms, cyano group, carboxyl group, hydroxymethyl group, phenyl group which may be substituted or benzoyl group, $R^6$ indicates a hydrogen atom, lower alkyl group having 1 to 3 carbon atoms or benzyl group; and X indicates a methylene group, or an acid or alkali salt thereof.

* * * * *